United States Patent
Fowler et al.

(10) Patent No.: US 11,013,231 B2
(45) Date of Patent: May 25, 2021

(54) CYCLOPROPENE COMPOSITIONS

(71) Applicant: SYNGENTA PARTICIPATIONS AG, Basel (CH)

(72) Inventors: Jeffrey David Fowler, Greensboro, NC (US); Sejong Kim, Greensboro, NC (US)

(73) Assignee: SYNGENTA PARTICIPATIONS AG, Basel (CH)

( * ) Notice: Subject to any disclaimer, the term of this patent is extended or adjusted under 35 U.S.C. 154(b) by 0 days.

(21) Appl. No.: 16/263,938

(22) Filed: Jan. 31, 2019

(65) Prior Publication Data

US 2019/0159447 A1 May 30, 2019

Related U.S. Application Data

(62) Division of application No. 13/702,263, filed as application No. PCT/US2011/039461 on Jun. 7, 2011, now Pat. No. 10,206,389.

(60) Provisional application No. 61/352,252, filed on Jun. 7, 2010.

(51) Int. Cl.

| | | |
|---|---|---|
| A01N 25/04 | (2006.01) | |
| A01N 25/02 | (2006.01) | |
| C05G 3/00 | (2020.01) | |
| B82Y 5/00 | (2011.01) | |
| A01N 27/00 | (2006.01) | |
| C05G 5/20 | (2020.01) | |

(52) U.S. Cl.
CPC ............. *A01N 25/04* (2013.01); *A01N 25/02* (2013.01); *A01N 27/00* (2013.01); *B82Y 5/00* (2013.01); *C05G 3/00* (2013.01); *C05G 5/20* (2020.02)

(58) Field of Classification Search
CPC ........ A01N 25/04; A01N 25/02; A01N 27/00; C05G 3/00; B82Y 5/00
See application file for complete search history.

(56) References Cited

U.S. PATENT DOCUMENTS

| | | | | |
|---|---|---|---|---|
| 3,462,393 A | ‡ | 8/1969 | Legler ............... | C08L 63/00 525/40 |
| 6,548,448 B2 | ‡ | 4/2003 | Kostansek ............ | A01N 3/00 206/42 |
| 6,743,756 B2 | ‡ | 6/2004 | Harris, Jr. ............ | A01N 25/04 106/17 |
| 6,849,575 B2 | ‡ | 2/2005 | Haesslin ............. | A01N 43/40 504/10 |
| 6,936,572 B2 | ‡ | 8/2005 | Stewart .............. | A01N 25/04 504/362 |
| 7,019,052 B1 | ‡ | 3/2006 | Rink ................ | C08F 2/06 523/456 |
| 8,946,122 B2 | ‡ | 2/2015 | Fowler .............. | A01N 25/04 504/124 |
| 10,206,389 B2 | * | 2/2019 | Fowler .............. | C05G 5/20 |
| 2002/0193256 A1 | ‡ | 12/2002 | Harris, Jr. | |

FOREIGN PATENT DOCUMENTS

| | | | |
|---|---|---|---|
| EP | 1787513 | ‡ | 5/2007 |
| EP | 2020177 | ‡ | 2/2009 |
| WO | 2008030749 | | 3/2008 |
| WO | WO 2008030749 | ‡ | 3/2008 |
| WO | 2008089140 | | 7/2008 |
| WO | WO-2008/089140 | ‡ | 7/2008 |
| WO | WO-2008089140 | ‡ | 7/2008 |
| WO | 2010080891 | | 7/2010 |
| WO | WO-2010/080891 | ‡ | 7/2010 |
| WO | 2011109144 | | 9/2011 |
| WO | WO-2011/109144 | ‡ | 9/2011 |

OTHER PUBLICATIONS

Extended European Search Report dated Sep. 3, 2014.‡

* cited by examiner
‡ imported from a related application

*Primary Examiner* — Mina Haghighatian

(74) *Attorney, Agent, or Firm* — Baker & Hostetler LLP; Toni-Junell Herbert

(57) ABSTRACT

Stabilized liquid cyclopropane compositions are provided which compromise flowable, non-aqueous dispersion concentrates comprising a) a continuous substantially water-immiscible liquid phase and b) a dispersed solid phase comprising cured polymer particles prepared from a polymerizable thermoset resin which particles contain at least one cylcopropene complex, optionally a non-porous particulate mineral, and optionally a non-cross-linkable mobile chemical distributed therein, and wherein the outside surfaces of the particles comprise a colloidal solid material. The compositions of the invention can be used directly or with dilution to combat pests or as plant growth regulators.

10 Claims, No Drawings

CYCLOPROPENE COMPOSITIONS

This application is a divisional application of U.S. application Ser. No. 13/702,263 filed May 7, 2013, which is the national phase of International Application No. PCT/US2011/039461, filed Jun. 7, 2011, which claims priority to U.S. Provisional Application No. 61/352,252, filed Jun. 7, 2010, the entire contents of all of which are hereby incorporated by reference.

BACKGROUND OF THE INVENTION

It is known that ethylene is involved in plant senescence and plant stress reactions. For this reason, plant growth regulators (PGRs) that inhibit or regulate the production of ethylene or control its action in plants have been developed in an effort to improve the economic yield of agricultural crops.

In practice, such PGRs may be applied to plants in a variety of methods including different formulations. Of these various methods, use of liquid and dry compositions are the most common. The particular formulation desired and the resulting effect on the physiology of plant growth will greatly depend upon the PGR used, the plant species to be treated, environmental conditions, the geographical area and the climate of the area at the time of treatment.

Certain obstacles make the actual use of some PGRs impractical in certain circumstances. For example, one group of ethylene inhibitor PGRs are the cyclopropenes which are mainly gaseous small molecules. One example of such a cyclopropene PGR is 1-methylcyclopropene (1-MCP), which is often employed in the form of a complex with a molecular encapsulating agent as a way of more conveniently storing, transporting and delivering the 1-MCP to a target plant or to soil. Contact between such 1-MCP complexes and water will quickly release 1-MCP gas from the complex in order to accomplish delivery of the PGR to the target.

A challenge arises where a user of a concentrate formulation containing a 1-MCP complex wishes to dilute the formulation in water (for example in a spray tank) in order to form an aqueous spray composition. Such aqueous agrochemical spray compositions are widely used in agriculture, but their performance with 1-MCP complexes sometimes can be limited by the tendency for the 1-MCP complex to degrade in a spray tank on exposure to water. This can result in reduced efficacy and in an unacceptable build-up of the 1-MCP gas in the head-space of the spray tank.

In addition, due to the relatively complex supply chain for crop protection agents, such 1-MCP complex containing concentrates can be stored for long periods and may be subjected during storage and shipping to extreme temperature variations, high-shear, repetitive vibration patterns and to humidity. Such supply chain conditions can increase the likelihood of formulation failure due to, for example, water mediated degradation and stability problems.

Considering the variety of conditions and special situations under which 1-MCP complex containing concentrates are stored, shipped and used around the world, there remains a need for concentrate formulations of 1-MCP that provide stability benefits under at least some of those conditions and situations. There is a further need for such concentrate formulations having high loading, that are stable for a period of time when diluted with water under a wide range of field conditions, and wherein an end user may control the release rate of the 1-MCP into the application site from a concentrate or dilute spray formulation.

SUMMARY OF THE INVENTION

Stabilized, liquid cyclopropene compositions are provided which comprise flowable, non-aqueous dispersion concentrates comprising a) a continuous non-aqueous substantially water-immiscible liquid phase and b) a dispersed solid phase comprising polymer particles prepared from a curable or polymerizable resin, wherein the outside surfaces of the polymer particles comprise a colloidal solid material and wherein the polymer particles have at least one solid complex of a cyclopropene gas with a molecular encapsulating agent distributed within the dispersed phase. In one embodiment, the colloidal solid material is present in the dispersed solid phase in an amount effective to stabilize the resin in an emulsion state during the process which is used to prepare the dispersed phase. In another embodiment the polymer particles also contain a non-cross-linkable mobile chemical such that the extraction of this chemical from the dispersed solid phase renders it porous in a manner that allows the cyclopropene gas or complex to diffuse out from the dispersed phase in a controlled rate. In another embodiment the polymer particles also contain a non-porous particulate mineral as a diffusion barrier. The cyclopropene compositions of the invention can be used directly or with dilution as plant growth regulators.

In accordance with the invention, it has been found that non-aqueous dispersion concentrates of solid complexes of a cyclopropene gas and a molecular encapsulating agent in a non-aqueous, substantially water-immiscible liquid can be prepared by using curable or polymerizable resin polymers to entrap the cyclopropene complex in a polymer matrix where a colloidal solid is used to stabilize the polymer resin in an emulsion state during the process which is used to prepare the dispersed phase. The cyclopropene complex can be distributed within the curable or polymerizable resin polymer matrix which is dispersed as particles within the continuous water-immiscible liquid phase. Other active ingredients may optionally be dispersed, dissolved or suspended within the continuous phase. The release rate of the cyclopropene from the dispersed solid phase can be controlled by the optional incorporation within the dispersed phase of mobile non-cross-linkable molecules, where these molecules are chosen to be miscible with the un-cured or un-polymerized resin that will form the particulate polymer matrix, soluble in water or some other medium to which the solid polymer particles will be exposed, and of molecular dimensions such that the voids they create in the dispersed phase upon extraction, allow the desired release of the cyclopropene. The non-aqueous dispersion concentrates of the invention have a usefully long period of protection for the encapsulated cyclopropene gas which provides a practical utility in terms of storage, shipment and use. The dispersion concentrates of the invention also provide the ability to control the release rate of the cyclopropene gas into the target site from the concentrate or an end-use dilute formulation.

The polymerizable resins suitable for use in preparing the dispersed phase polymer matrix can be selected from monomers, oligomers or prepolymers that are curable or polymerizable to thermoset or thermoplastic polymers.

The present invention further relates to polymer particles comprising an entrapped solid complex of a cyclopropene gas with a molecular encapsulating agent that is either homogeneously or non-homogeneously distributed within such polymer particles or present in the form of domains within such particles and wherein the outside surface regions of the particles comprise a colloidal solid material.

The curable or polymerizable resins used to prepare the polymer matrix can be chosen to be sufficiently hydrophobic such that, when the concentrate is diluted into water to form an aqueous spray solution, the particles of the cured or polymerized resin polymer matrix protect the cyclopropene complex distributed therein from exposure to water for a period of time depending principally on the size of the dispersed polymer particle and the polarity and porosity of the polymer matrix. In an embodiment, the cyclopropene complex is homogeneously distributed in the polymer matrix or is present in the form of domains within the polymer matrix or particles thereof. One skilled in the art will readily determine the optimum particle size of the solid phase within the scope of the current invention that is sufficient for the desired end-use application. One skilled in the art will also readily determine the optimum porosity of the polymer matrix, for example, through the selection of cross-linkable or polymerizable monomers that form a suitable polymer matrix with appropriate cross-link density and crystallinity, through the incorporation within the matrix of mobile non-cross-linkable molecules that dissolve and diffuse out of the matrix, and/or through the incorporation within the matrix of a nonporous particulate mineral as a diffusion barrier. Those skilled in the art will also be able to select suitable monomers, oligomers or prepolymers which are polymerizable to either a thermoset or thermoplastic polymer matrix with an appropriate composition of hydrophobic and hydrophilic chemical groups to optimize the polarity of the polymer matrix.

The present invention also includes a method for regulating the growth of plants at a locus such as soil or foliage which comprises treating said locus with a dispersion concentrate according to the invention or dispersing a concentrate according to the present invention in water and treating said locus with the obtained diluted aqueous end-use formulation.

DETAILED DESCRIPTION OF THE INVENTION

Accordingly, in one embodiment, the non-aqueous liquid dispersion concentrate compositions of the present invention comprise:
a) a continuous, substantially water-immiscible, non-aqueous liquid phase, optionally comprising at least one agrochemically active ingredient; and
b) a dispersed, solid phase comprising polymer particles prepared from a curable or polymerizable thermoset or thermoplastic resin, wherein the outer surfaces of the polymer particles comprise a colloidal solid material in an amount effective to stabilize the resin in an emulsion state during the process which is used to prepare the dispersed phase and wherein the polymer particles have at least one solid complex of a cyclopropene gas and a molecular encapsulating agent distributed therein.

The curable or polymerizable thermoset resins suitable for use in the dispersed solid phase are understood to include all molecules that may be irreversibly polymerized or cured to form a polymeric matrix that does not melt or deform at elevated temperatures below the point of thermal decomposition. The polymerization reaction may be initiated thermally, by addition of chemical curing agents or by suitable irradiation to create radicals or ions such as by visible, UV, microwave or other electromagnetic irradiation, or electron beam irradiation. Examples include the phenolics, ureas, melamines, epoxies, polyesters, silicones, rubbers, polyisocyanates, polyamines and polyurethanes. In addition, bio-derived or biodegradable thermoset resins may be noted including epoxy or polyester resins derived from natural materials such as vegetable oil, soy, wood and the like.

In one embodiment, the dispersion concentrates for use in the liquid agrochemical compositions of the present invention are those that are formed using curing agents, monomers, oligomers, prepolymers or blends thereof that exhibit a slow curing or polymerization reaction when combined with the curing agents at ambient conditions. Particularly suitable are those curing agents, monomers, oligomers, prepolymers or blends thereof that exhibit no significant increase in viscosity under ambient conditions for a period of at least 15 minutes, more particularly 30 minutes, most particularly 1 hour, after mixing with the curing agent.

The polymerizable resins suitable for use in the invention can also be chosen to be sufficiently hydrophobic such that, when the concentrate is diluted into water to form an aqueous spray solution, the particles of the cured polymer matrix protect the cyclopropene complex distributed therein from exposure to water for a period of time depending principally on the size of the dispersed polymer particle, and the polarity and porosity of the polymer matrix.

Those skilled in the art will readily determine the optimum particle size for cured polymer particles use within the scope of the current invention that is sufficient for the desired end-use application. In one embodiment, the polymer particles of the dispersed solid phase b) have a mean particle size of from 1 to 200 microns, more particularly from 1 to 100 microns and most particularly, from 2 to 80 microns. In the context of the present invention, mean particle size means the volume-weighted mean, commonly designated D(v,0.5).

In one embodiment, suitable polymerizable resins are those that are substantially immiscible with the non-aqueous liquid used in the continuous phase.

In one embodiment, suitable cyclopropenes are gaseous at ambient temperature and are selected from a compound of formula I:

$$(R)n\text{---}\triangle \qquad (I)$$

Wherein n is a number from 1 to 4, suitably n is a number from 1 to 2, and most suitably n is 1. The variable group R is selected from hydrogen, saturated or unsaturated $C_1$ to $C_4$ alkyl, hydroxy, halogen, alkoxy, amino and carboxy. In one embodiment, R is methyl.

In one embodiment, the cyclopropene gas is selected from cyclopropene, dimethylcyclopropene and 1-methylcyclopropene (1-MCP).

In one embodiment, the suitable molecular encapsulating agents for the gaseous cyclopropenes PGRs include cyclodextrins, crown ethers, polyoxyalkylenes, prophorines, polysiloxanes, phophazenes, cucurbiturils and zeolites. In another embodiment, a suitable molecular encapsulating agent is a-cyclo dextrin.

The solid complex of the cyclopropene gas and a molecular encapsulating agent is sometimes referred to herein as a "cyclopropene complex".

For example, in one method of making a cyclopropene complex in which 1-MCP is encapsulated in a molecular encapsulating agent, the 1-MCP gas is bubbled through a solution of a-cyclodextrin in water, from which the complex first precipitates and is then isolated by filtration. Cyclopropene complexes made by the above method are isolated, dried and stored in solid form, for example as an active ingredient containing powder, for later addition to the inventive dispersion concentrates.

As noted above, in an embodiment, the cyclopropene complex is homogeneously distributed in the particles of the polymer matrix or network that is formed from curing or polymerizing the thermoset or thermoplastic monomers, oligomers, prepolymers and/or hardeners. Alternatively, the cyclopropene complex is present in such particles in the form of domains within such polymer matrix or network. In one embodiment, the domains are open cells within the polymer matrix. In another embodiment, the domains are closed cells within the polymer matrix.

In one embodiment, the non-aqueous liquids suitable for use in the continuous phase a) are substantially immiscible with water and the affinity of the liquid for the cyclopropene complex distributed in the dispersed solid phase must be such that substantially all of the cyclopropene complex remains in the dispersed solid phase and substantially none migrates to the continuous phase. Those skilled in the art will readily be able to determine whether a particular water-immiscible liquid meets this criterion for the cyclopropene complex in question by following any standard test procedure for determining the partition coefficient of a material (in this case, the cyclopropene complex) between the continuous liquid phase and the dispersed solid phase. Accordingly, in one embodiment, the dispersed solid phase b) is immiscible with the continuous phase a).

Examples of water-immiscible, non-aqueous liquids suitable for use in the continuous phase a) include: petroleum distillates, vegetable oils, silicone oils, methylated vegetable oils, refined paraffinic hydrocarbons (such as ISOPAR V, for example), mineral oils, alkyl amides, alkyl lactates, alkyl acetates, or other liquids and solvents with a log P of 3 or above, and mixtures thereof. In one embodiment, the water-immiscible, non-aqueous liquid used in the continuous phase a) has a log P of about 4 or above.

In another embodiment, the non-aqueous liquids suitable for use in the continuous phase a) are substantially water-immiscible. In the context of the invention, the term "substantially water-immiscible" means a non-aqueous liquid that forms two phases when mixed with water at a concentration below 10 wt %.

In one embodiment of the invention, the dispersed solid phase b) comprises a cured or polymerized thermoset or thermoplastic resin polymer with sufficient hydrophobicity so that when the concentrate is emulsified upon dilution with water, the particles of such polymer matrix continue to protect the cyclopropene complex from exposure to water in the diluted aqueous spray formulation for a period well within the acceptable range for such dilutions that are to be used for agricultural spray applications.

For example, in one embodiment, a major amount of a cyclopropene complex can be protected from exposure to water for more than about 1 hour in an agitated spray tank.

In one embodiment, when the concentrate is diluted in water, some of the cyclopropene slowly diffuses out of the polymer particles. The cyclopropene release rate from the diluted aqueous spray formulation in the spray tank can be adjusted, for example, by varying the size of the dispersed polymer particles in the concentrate, the concentration of cyclopropene complex in the polymer particles, the pH of the spray tank dispersion, the optional inclusion of a non-cross-linkable mobile chemical within the polymer particles, the optional inclusion of non-porous particulate minerals as a diffusion barrier within the polymer particles, and the amount and nature of the curable or polymerizable thermoset or thermoplastic resin including monomers, oligomers, prepolymers and hardeners used to form the polymer particles.

The cyclopropene release rate of from the dispersed solid phase can be further controlled by the optional incorporation within the dispersed phase of non-porous particulate minerals as a diffusion barrier. For purposes of the present invention, non-porous means that the mineral lacks pores larger than individual molecules of the cyclopropene, such that the diffusion coefficient of the cyclopropene through particles of the mineral is less than $10^{-15}$ $m^2/s$.

In this regard, the dispersed phase can also include one or more non-cross-linkable mobile chemicals such that the extraction of this chemical from the dispersed phase renders it porous in a manner that allows the cyclopropene active ingredient to diffuse out from the disperse phase. Examples include acids, bases, surfactants, polymers, copolymers, substantially water-soluble compounds or substantially water-insoluble compounds.

The non-cross-linkable mobile chemical in the dispersed phase may optionally be selected to also perform as a surfactant or dispersant within the liquid dispersion concentrate that is used to prepare the end-use liquid agrochemical compositions of the present invention. If selected in this manner, the mobile chemical will adsorb to the surfaces of polymer particles present in the dispersion concentrate and thereby stabilize the dispersion of those polymer particles. This behavior will be observable in at least one of the following ways: the polymer particles will be distributed individually rather than as agglomerates within the dispersion concentrate when observed microscopically, the viscosity of the dispersion concentrate will be reduced when the mobile chemical is added, or the polymer particles will have a greater tendency to remain within the dispersed phase instead of being lost to the continuous phase when liquid agrochemical end-use compositions are prepared. Examples of suitable water-insoluble polymers useful for this purpose include copolymers of an a-olefin and an N-vinylpyrrolidone such as, for example, alkylated vinylpyrrolidone copolymers such as the Agrimers (e.g., Agrimer® AL-22, based on 1-ethenylhexadecyl-2-pyrrolidinone) (International Specialty Products (ISP) Corporation), or copolymers of an a-olefin and ethylene glycol such as, for example Atlox 4914 of Croda Corp.

In one embodiment, the non-aqueous liquid dispersion concentrate compositions of the present invention comprise the solid phase in the form of finely divided suspended polymer/cyclopropene complex particles comprising a colloidal solid material at their surface and containing at least one cyclopropene complex, where the mean particle diameter of such polymer particles is generally below 200 microns, frequently below 100 microns, for example in the range from 1-200, particularly in the range from 1-100 and especially in the range from 2-80 microns.

In one embodiment, the colloidal solid material is a Pickering colloid emulsion stabilizer.

In the context of the present invention, a colloidal solid material is one whose properties of interest are determined by its surface interactions with other materials. Colloidal solids are therefore necessarily those with high specific surface area, typically above 10 $m^2/g$. For example, colloidal solids are able to stabilize emulsions of immiscible liquids, as described for instance in WO 2008/030749. When serving for this purpose, such colloidal solids may be called Pickering colloids, colloidal emulsion stabilizers, or other equivalent terms. Functional tests are known for whether a colloidal solid can stabilize a resin in an emulsion state during the curing reaction as used herein. One such test is described infra in paragraph 97 below. Not all colloidal solids are able to stabilize any given pair of immiscible liquids, and such a functional test may used by those skilled in the art to identify a suitable colloid.

As noted above, the cyclopropene release rate from the dispersed solid phase can be further controlled by the optional incorporation within the disperse phase of nonporous particulate minerals as a diffusion barrier. In some circumstances the same nonporous particulate mineral used as a diffusion barrier within the disperse phase may also serve as the colloidal emulsion stabilizer. In this situation the particulate mineral may be added in two separate points within the preparation process as described below—firstly to the dispersed phase concentrate in order to become incorporated within the particles of the dispersed phase, and secondly to the continuous phase in order to stabilize the resin in an emulsion state during the curing or polymerization reaction.

In some cases the spontaneity, and stability of the polymer particles of the dispersed phase b) against flocculation on dilution with water, can be improved, by adding one or more emulsifiers to the continuous water-immiscible non-aqueous solvent phase of the dispersion concentrate. Examples of suitable emulsifiers which serve in this manner include: phosphate esters of ethoxylated tristyrylphenol (such as Soprophor 3D33 of Rhodia), polyalkoxylated alcohols such as Rhodasurf BC-610 of Rhodia or polyalkoxylated (4 mole EO) sorbitan mono-oleate (Tween 21 of Croda).

In another embodiment, the overall physical stability, flowability and handling properties of the dispersion concentrate can be improved by adding one or more surfactants or dispersants to the continuous water-immiscible non-aqueous solvent phase, including polyvinylpyrrolidone (Agrimer 90 of ISP), acetic acid ethenyl ester polymer with 1-ethenyl-2-pyrrolidone (Agrimer VA 51 of ISP), and non-ionic surfactants. For example, suitable nonionic surfactants are those that are hydrophilic with an HLB above about 12, such as Atplus MBA 13/30 of Croda, amine based block copolymers such as Tertronic 1107 of BASF, or polyalkoxylated butanol (Toximul 8320 of Stepan).

As used herein, the term "degradation" in relation to the cyclopropene complex denotes release of the cyclopropene active ingredient, i.e., the water-soluble, water-dispersible or water-sensitive agrochemical from the molecular encapsulating agent, as well as chemical degradation of the agrochemical, as a result of contact with water. Degradation can be determined simply by measuring the amount of the cyclopropene present before and after contact with water.

The term "agrochemical active ingredient" associated with optional use in the continuous phase a) refers to chemicals and biological compositions, such as those described herein, which are effective in killing, preventing, or controlling the growth of undesirable pests, such as, plants, insects, mice, microorganism, algae, fungi, bacteria, and the like (such as pesticidally active ingredients). The term may also apply to compounds that control the growth of plants in a desired fashion (e.g., plant growth regulators), to a compound which mimics the natural systemic activated resistance response found in plant species (e.g., plant activator) or to a compound that reduces the phytotoxic response to a herbicide (e.g., a safener). If more than one is present, the agrochemically active ingredients are independently present in an amount that is biologically effective when the composition is diluted, if necessary, in a suitable volume of liquid carrier, e.g., water, and applied to the intended target, e.g., to the foliage of a plant, to the locus thereof or to the soil where cultivation of such plants is intended.

Examples of optional agrochemical active ingredients suitable for use within the continuous phase a) in accordance with the present invention include, but are not limited to: fungicides such as azoxystrobin, chlorothalonil, cyprodinil, difenoconazole, fludioxonil, mandipropamid, picoxystrobin, propiconazole, pyraclostrobin, tebuconazole, thiabendazole and trifloxystrobin; herbicides such as acetochlor, alachlor, ametryn, anilofos, atrazine, azafenidin, benfluralin, benfuresate, bensulide, benzfendizone, benzofenap, bromobutide, bromofenoxim, bromoxynil, butachlor, butafenacil, butamifos, butralin, butylate, cafenstrole, carbetamide, chloridazon, chlorpropham, chlorthal-dimethyl, chlorthiamid, cinidon-ethyl, cinmethylin, clomazone, clomeprop, cloransulam-methyl, cyanazine, cycloate, desmedipham, desmetryn, dichlobenil, diflufenican, dimepiperate, dimethachlor, dimethametryn, dimethenamid, dimethenamid-P, dinitramine, dinoterb, diphenamid, dithiopyr, EPTC, esprocarb, ethalfluralin, ethofumesate, etobenzanid, fenoxaprop-ethyl, fenoxaprop-P-ethyl, fentrazamide, flamprop-methyl, flamprop-M-isopropyl, fluazolate, fluchloralin, flufenacet, flumiclorac-pentyl, flumioxazin, fluorochloridone, flupoxam, flurenol, fluridone, flurtamone, fluthiacet-methyl, indanofan, isoxaben, isoxaflutole, lenacil, linuron, mefenacet, mesotrione, metamitron, metazachlor, methabenzthiazuron, methyldymron, metobenzuron, metolachlor, metosulam, metoxuron, metribuzin, molinate, naproanilide, napropamide, neburon, norflurazon, orbencarb, oryzalin, oxadiargyl, oxadiazon, oxyfluorfen, pebulate, pendimethalin, pentanochlor, pethoxamid, pentoxazone, phenmedipham, pinoxaden, piperophos, pretilachlor, prodiamine, profluazol, prometon, prometryn, propachlor, propanil, propazine, propham, propisochlor, propyzamide, pro sulfocarb, pyraflufen-ethyl, pyrazogyl, pyrazolynate, pyrazoxyfen, pyributicarb, pyridate, pyriminobac-methyl, quinclorac, siduron, simazine, simetryn, S-metolachlor, sulcotrione, sulfentrazone, tebutam, tebuthiuron, terbacil, terbumeton, terbuthylazine, terbutryn, thenylchlor, thiazopyr, thidiazimin, thiobencarb, tiocarbazil, triallate, trietazine, trifluralin, and vernolate; herbicide safeners such as benoxacor, dichlormid, fenchlorazole-ethyl, fenclorim, flurazole, fluxofenim, furilazole, isoxadifen-ethyl, mefenpyr; alkali metal, alkaline earth metal, sulfonium or ammonium cation of mefenpyr; mefenpyr-diethyl and oxabetrinil; insecticides such as abamectin, clothianidin, emamectin benzoate, gamma cyhalothrin, imidacloprid, lambda cyhalothrin, permethrin, resmethrin and thiamethoxam.

In one embodiment, the active ingredients in the continuous phase a) may be in the state of a solution, an emulsion, a microemulsion, a microcapsule, a particle and/or a fine particle that is readily suspended in the liquid. In the context of the present invention, a fine particle is one substantially smaller than the dimensions of the solid polymeric particles of the dispersed phase, such that a plurality (at least 10) of active ingredient particles are within each particle of the dispersed phase, whereas a non-fine particle is one only slightly smaller than the dimensions of the solid polymeric particles of the dispersed phase, such that each polymeric particle contains only a few active ingredient particles.

Further aspects of the invention include a method of preventing or combating infestation of plant species by pests, and regulating plant growth by diluting an amount of the non-aqueous liquid dispersion concentrate composition with a suitable liquid carrier, such as water or liquid fertilizer, and applying the dilute formulation to the plant, tree, animal or locus as desired. The concentrate formulations of the present invention may also be combined in a continuous flow apparatus with water in spray application equipment, such that no holding tank is required for the diluted product.

The non-aqueous liquid dispersion concentrate compositions can be stored conveniently in a container from which they are poured, or pumped, or into which a liquid carrier is added prior to application.

The advantages of the non-aqueous liquid dispersion concentrate compositions of the present invention include: storage-stability for extended periods, for example 6 months or longer at room temperature; simple handling is made possible for users because dilution is made with water, or other liquid carrier, for preparation of application mixtures; reduced degradation of the cyclopropene complex; reduced settling of the suspension during storage or on dilution; the compositions can easily be resuspended or redispersed with only a minor amount of agitation.

The rate of application of the composition of the invention will depend on a number of factors including, for example, whether or not any optional agrochemical active ingredients are chosen for use, the identity of the pest to be controlled or the plants whose growth is to be regulated and the formulations selected for use and whether the compound is to be applied to foliage, soil, for root uptake or by chemigation. As a general guide, however, an application rate of from 1 to 2000 g active ingredient per hectare is suitable, in particular from 2 to 500 g active ingredient per hectare. For 1-MCP and plant growth regulators, use rates are about 0.1 to 50 g per hectare.

In one embodiment, suitable rates for the optional agrochemically active ingredients used in the inventive compositions are comparable to the existing rates given on the current product labels for products containing such actives. For example, Quadris$^{(m)}$ brand azoxystrobin can be applied at a rate of from 112 g to 224 g a.i./hectare and Quilt™ brand premix of azoxystrobin (75 g/L)/propiconazole (125 g/L) can be applied at a rate of from 0.75-1.5 L/ha.

In one embodiment of the present invention, the dispersion concentrate composition comprises a cyclopropene complex and this cyclopropene complex is distributed within a polymer particle that is itself dispersed within a continuous substantially water-immiscible liquid phase, thus forming an oil dispersion concentrate of a solid-in-oil.

As used herein, the term "agrochemically effective amount" means the amount of an agrochemical active compound which adversely controls or modifies target pests or regulates the growth of plants (PGR). For example, in the case of herbicides, a "herbicidally effective amount" is that amount of herbicide sufficient for controlling or modifying plant growth. Controlling or modifying effects include all deviation from natural development, for example, killing, retardation, leaf burn, albinism, dwarfing and the like. The term plants refers to all physical parts of a plant, including seeds, seedlings, saplings, roots, tubers, stems, stalks, foliage and fruits. In the case of fungicides, the term "fungicide" shall mean a material that kills or materially inhibits the growth, proliferation, division, reproduction, or spread of fungi. As used herein, the term "fungicidally effective amount" or "amount effective to control or reduce fungi" in relation to the fungicidal compound is that amount that will kill or materially inhibit the growth, proliferation, division, reproduction, or spread of a significant number of fungi. As used herein, the terms "insecticide", "nematicide" or "acaricide" shall mean a material that kills or materially inhibits the growth, proliferation, reproduction, or spread of insects, nematodes or acarids, respectively. An "effective amount" of the insecticide, nematicide or acaricide is that amount that will kill or materially inhibit the growth, proliferation, reproduction or spread of a significant number of insects, nematodes or acarides.

In one aspect, as used herein, "regulating (plant) growth", "plant growth regulator", PGR, "regulating" or "regulation" provided by a PGR present in the dispersion concentrate includes the following plant responses; inhibition of cell elongation, for example reduction in stem height and internodal distance, strengthening of the stem wall, thus increasing the resistance to lodging; compact growth in ornamentals for the economic production of improved quality plants; promotion of better fruiting; increasing the number of ovaries with a view to stepping up yield; promotion of senescence of the formation of tissue enabling fruit to absciss; defoliation of nursery and ornamental bushes and trees for marl-order business in the fall; defoliation of trees to interrupt parasitic chains of infection; hastening of ripening, with a view to programming the harvest by reducing the harvest to one to two pickings and interrupting the food-chain for injurious insects.

The cyclopropene gases present in the dispersion concentrate are PGRs that act as ethylene-binding inhibitors. One well-known such cyclopropene gas is 1-methylcyclopropene (MCP). 1-MCP prevents the signal from ethylene to initiate stress responses in plants and which inhibits the sensitivity of plants or plant parts (e.g. fruits and flowers) to ethylene by inhibiting its perception. Consequently, in another aspect, "regulating the growth", "regulating (plant) growth", "plant growth regulator", "PGR", "regulating" or "regulation" also includes the use of a water dispersible dispersion concentrate composition as defined according to the present invention for increasing the yield and/or improving the vigor of an agricultural plant. According to one embodiment of the present invention, the inventive compositions are used for improved tolerance against biotic stress factors such as fungi, bacteria, viruses and/or insects and abiotic stress factors such as heat stress, nutrient stress, cold stress, drought stress, UV stress and/or salt stress of an agricultural plant.

The selection of application rates relative to providing a desired level of pesticidal and/or plant growth regulating activity for a composition of the invention is routine for those skilled in the art to optimise the bioperformance of the active ingredient concerned. Application rates will depend on factors such as level of pest pressure, plant conditions, weather and growing conditions as well as the activity of the agrochemically active ingredients and any applicable label rate restrictions.

The invention relates also to liquid agrochemical compositions comprising
  a) a continuous, substantially water-immiscible, non-aqueous liquid phase, optionally comprising at least one agrochemically active ingredient (for example, in the state selected from a solution or a dispersion such as emulsion, a microemulsion, or a suspension of microcapsules or fine particles); and
  b) a dispersed, solid phase comprising polymer particles prepared from a curable or polymerizable thermoset or thermoplastic resin, wherein the outside surfaces of the polymer particles comprise a colloidal solid material in an amount effective to stabilize the resin in an emulsion state during the curing or polymerization reaction and wherein the polymer particles have at least one cyclopropene complex distributed therein.

A further aspect of the invention relates to a dilute aqueous spray composition for regulating the growth of plants at a locus comprising
 a) a continuous aqueous phase comprising a suitable liquid carrier, such as water or liquid fertilizer, in an amount sufficient to obtain the desired final concentration of the agrochemical active ingredients in the spray composition;
 b) a dispersed solid phase comprising polymer particles prepared from a curable or polymerizable thermoset or thermoplastic resin, wherein the outside surfaces of the particles comprise a colloidal solid material in an amount effective to stabilize the resin in an emulsion state during the curing or polymerization reaction and wherein the polymer particles have at least one cyclopropene complex distributed therein; and
 c) optionally at least one agrochemically active ingredient dispersed, dissolved, suspended, microemulsified or emulsified in the liquid carrier.

In another embodiment, the invention relates to a dilute composition for ultra low volume (ULV) application comprising:

a) a continuous phase comprising a carrier solvent having a flash point above 55° C. in an amount sufficient to obtain the desired final concentration of each of the agrochemically active ingredients in the ULV composition;

b) a dispersed solid phase comprising polymer particles prepared from a curable or polymerizable thermoset or thermoplastic resin, wherein the outside surfaces of the particles comprise a colloidal solid material in an amount effective to stabilize the resin in an emulsion state during the curing or polymerization reaction and wherein the particles have at least one cyclopropene complex distributed therein.

The invention relates also to a method for combating or preventing pests in crops of useful plants or regulating the growth of such crops, said method comprising:

1) treating the desired area, such as plants, the plant parts or the locus thereof with a concentrate composition comprising:

a) a continuous substantially water-immiscible, non-aqueous liquid phase, optionally comprising at least one agrochemically active ingredient;

b) a dispersed solid phase comprising polymer particles prepared from a curable or polymerizable thermoset or thermoplastic resin, wherein the outside surfaces of the particles comprise a colloidal solid material in an amount effective to stabilize the resin in an emulsion state during the curing or polymerization reaction and wherein the particles have at least one cyclopropene complex distributed therein; and 2) diluting the concentrate composition, if necessary, in a suitable carrier, such as water, aqueous liquid fertilizer or a carrier solvent having a flash point above 55° C., in an amount sufficient to obtain the desired final concentration of each of the agrochemically active ingredients; and then treating the desired area, such as plants, the plant parts or the locus thereof with the dilute spray or ULV composition.

The term plants refers to all physical parts of a plant, including seeds, seedlings, saplings, roots, tubers, stems, stalks, buds, flowers, foliage and fruits. The term locus refers to where the plant is growing or is expected to grow.

The composition according to the invention is suitable for all methods of application conventionally used in agriculture, e.g. pre-emergence application, post-emergence application and seed dressing. The compositions according to the invention are suitable for pre- or post-emergence applications to crop areas.

The compositions according to the invention are suitable especially for combating and/or preventing pests in crops of useful plants or for regulating the growth of such plants. Preferred crops of useful plants include canola, cereals such as barley, oats, rye and wheat, cotton, maize, soya, sugar beets, fruits, berries, nuts, vegetables, flowers, trees, shrubs and turf. The components used in the composition of the invention can be applied in a variety of ways known to those skilled in the art, at various concentrations. The rate at which the compositions are applied will depend upon the particular type of pests to be controlled, the degree of control required, and the timing and method of application.

Crops are to be understood as also including those crops which have been rendered tolerant to herbicides or classes of herbicides (e.g. ALS-, GS-, EPSPS-, PPO-, ACCase and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTIN33B0 (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood to include those which are obtained by conventional methods of breeding or genetic engineering and contain so-called output traits (e.g. improved storage stability, higher nutritional value and improved flavour).

Other useful plants include turf grass for example in golf-courses, lawns, parks and roadsides, or grown commercially for sod, and ornamental plants such as flowers or bushes.

Crop areas are areas of land on which the cultivated plants are already growing or in which the seeds of those cultivated plants have been sown, and also areas of land on which it is intended to grow those cultivated plants.

Other active ingredients such as herbicide, plant growth regulator, algaecide, fungicide, bactericide, viricide, insecticide, rodenticide, acaricide, nematicide or molluscicide may be present in the emulsion formulations of the present invention or may be added as a tank-mix partner with the emulsion formulations.

The compositions of the invention may further comprise other inert additives. Such additives include thickeners, flow enhancers, wetting agents, antifoaming agents, biocides, lubricants, fillers, drift control agents, deposition enhancers, adjuvants, evaporation retardants, freeze protecting agents, insect attracting odor agents, UV protecting agents, fragrances, and the like. The thickener may be a compound that is soluble or able to swell in water, such as, for example, polysaccharides of xanthans (e.g., anionic heteropolysaccharides such as RHODOPOL® 23 (Xanthan Gum)(Rhodia, Cranbury, N.J.)), alginates, guars or celluloses; synthetic macromolecules, such as polyethylene glycols, polyvinyl pyrrolidones, polyvinyl alcohols, modified cellulose-based polymers, polycarboxylates, bentonites, montmorillonites, hectonites, or attapulgites. The freeze protecting agent may be, for example, ethylene glycol, propylene glycol, glycerol, diethylene glycol, saccharose, water-soluble salts such as sodium chloride, sorbitol, triethylene glycol, tetraethylene glycol, urea, or mixtures thereof. Representative anti-foam agents are polydialkylsiloxanes, in particular polydimethylsiloxanes, fluoroaliphatic esters or perfluoroalkylphosphonic/perfluoroalkylphosphonic acids or the salts thereof and mixtures thereof Preferred are polydimethylsiloxanes, such as Dow Corning® Antifoam A or Antifoam B. Representative biocides include 1,2-benzisothiazolin-3-one, available as PROXEL® GXL (Arch Chemicals).

The compositions of the invention may be mixed with fertilizers and still maintain their stability. The fertilizers may comprise, for example, sulfur, nitrogen, phosphorous, and/or potassium.

The compositions of the invention may be used in conventional agricultural methods. For example, the compositions of the invention may be mixed with water and/or fertilizers and may be applied preemergence and/or postemergence to a desired locus by any means, such as airplane spray tanks, direct injection spray equipment, knapsack spray tanks, cattle dipping vats, farm equipment used in ground spraying (e.g., boom sprayers, hand sprayers), and the like. The desired locus may be soil, plants, and the like.

In one embodiment, the dispersion concentrate is prepared by:
  a. dissolving or suspending the cyclopropene complex in a nonaqueous curable liquid mixture comprising at least one suitable curable or polymerizable thermosetting or thermoplastic resin (comprising monomers, oligomers, prepolymers or blends thereof), optionally a suitable hardener, catalyst or initiator, and one or more optional components selected from non-porous particulate minerals as diffusion barrier and/or non-crosslinkable mobile chemicals;
  b. emulsifying said solution or suspension into a water-immiscible, non-aqueous liquid to a mean droplet size of 1-200 microns, which liquid also contains a colloidal solid as (Pickering) emulsion stabilizer, and, optionally, certain suitable hardener, catalyst or initiator capable of diffusing into the dispersed uncured resin droplets; and
  c. effecting crosslinking, polymerization or cure of the curable or polymerizable thermoset or thermoplastic resin mixture to produce polymer particles having at least one cyclopropene complex distributed therein and colloidal solids at their surfaces in an amount effective to stabilize the resin in an emulsion state during the curing or polymerization reaction and that after curing/polymerizing are dispersed in the non-aqueous liquid.

In one embodiment, the dispersion concentrate is prepared by adding a premix of the dispersed phase to a premix of the continuous phase, wherein:
1) the premix of the dispersed phase is prepared by blending with a high shear mixer: at least one cyclopropene complex, at least one suitable thermoset resin monomer, oligomer, prepolymer or blend thereof, a suitable hardener, catalyst or initiator, an optional non-crosslinkable mobile chemical, and an optional non-porous particulate mineral as diffusion barrier;
2) the premix of the continuous phase is prepared by blending with low shear mixer: a substantially water-immiscible, non-aqueous liquid with a colloidal solid as an emulsion stabilizer.

The resulting mixtures of the dispersed phase premix and the continuous phase premix are stirred under high shear conditions for a suitable time to form a Pickering emulsion and then heated or exposed to light or other electromagnetic radiation conditions (UV, microwave), as needed, in order to polymerize the dispersed phase. The shear rate and duration of the emulsification may be readily determined by one skilled in the art, guided by the following observations: if the shear rate is too low, the emulsion and resulting polymer matrix particles are relatively coarse and may be larger than desired; if the shear rate is instead too high or of too long a duration, the emulsion stabilizing colloid eventually becomes so depleted from the continuous phase that any new interfacial surface between the dispersed and continuous phases is effectively unprotected, at which point rapid coalescence or heteroflocculation of the dispersed phase occurs and the Pickering emulsion is effectively lost.

In one embodiment, the cyclopropene complex may be milled to the desired particle size prior to dispersion within the polymerizable resin (monomers, oligomers, and/or prepolymers, etc.) that will form the polymer matrix particles. The solid may be milled in a dry state using an air-mill or other suitable equipment as necessary, to achieve the desired particle size. The particle size may be a mean particle size of about 0.2 to about 20 microns, suitably about 0.3 to about 15 microns, more suitably about 0.5 to about 10 microns.

In one embodiment, the mixture of the dispersed phase premix and the continuous phase premix is stirred under high shear conditions for 5-10 min and heated to a temperature of about 30-120° C. for about 0.1-10 hr in order to effect the curing reaction.

Suitable polymerizable resins for use in preparing the solid polymer particles of the dispersed solid phase include thermosets such as epoxy resins, phenolic resins, polyurea resins, polyurethane resins, aminoplast resins and polyester resins.

In one embodiment the suitable polymerizable resins for use in preparing the solid polymer particles of the dispersed solid phase are biodegradable or bio-derived including, for example, epoxy or polyester resins derived from natural materials such as vegetable oil, soy, wood and the like.

With respect to the epoxies, all customary di- and polyepoxide monomers, prepolymers or blends thereof are suitable epoxy resins for the practice of this invention. In one embodiment, suitable epoxy resins are those that are liquid at ambient temperature. The di- and polyepoxides may be aliphatic, cycloaliphatic or aromatic compounds. Typical examples of such compounds are the diglycidyl ethers of bisphenol A, the glycidyl ethers and 13-methylglycidyl ethers of aliphatic or cycloaliphatic diols or polyols, including those of hydrogenated bisphenol A, ethylene glycol, 1,2-propanediol, 1,3-propanediol, 1,4-butanediol, diethylene glycol, polyethylene glycol, polypropylene glycol, glycerol, trimethylolpropane or 1,4-dimethylolcyclohexane or of 2,2-bis(4-hydroxycyclohexyl)propane, the glycidyl ethers of di- and polyphenols, typically resorcinol, 4,4'-dihydroxydiphenylmethane, 4,4'-dihydroxydiphenyl-2,2-propane, novolaks and 1,1,2,2-tetrakis(4-hydroxyphenyl)ethane. Further examples are N-glycidyl compounds, including diglycidyl compounds of ethylene urea, 1,3-propylene urea or 5-dimethylhydantoin or of 4,4'-methylene-5,5'-tetramethyldihydantoin, or those such as triglycidyl isocyanurate.

Further glycidyl compounds of technical importance are the glycidyl esters of carboxylic acids, especially di- and polycarboxylic acids. Typical examples are the glycidyl esters of succinic acid, adipic acid, azelaic acid, sebacic acid, phthalic acid, terephthalic acid, tetraand hexahydrophthalic acid, isophthalic acid or trimellitic acid or of dimerised fatty acids.

Exemplary of polyepoxides that differ from glycidyl compounds are the diepoxides of vinylcyclohexene and dicyclopentadiene, 3-(3',4'-epoxycyclohexyl)-8,9-epoxy-2,4-dioxaspiro[5.5]undecane, the 3',4'-epoxycyclohexylmethyl ester of 3,4-epoxycyclohexanecarboxylic acid, butadiene diepoxide or isoprene diepoxide, epoxidized linoleic derivatives or epoxidized polybutadiene.

Other suitable epoxy resins are diglycidyl ethers or advanced diglycidyl ethers of dihydric phenols or dihydric aliphatic alcohols of 2 to 4 carbon atoms, preferably the diglycidyl ethers or advanced diglycidyl ethers of 2,2-bis (4-hydroxyphenyl)propane and bis(4-hydroxyphenyl)methane or a mixture of these epoxy resins. Biodegradable or bio-derived epoxies such as diglycidyl ethers of vegetable oils are also suitable for use in the present invention.

Suitable epoxy resin hardeners for the practice of this invention may be any suitable epoxy resin hardener, typically selected from primary and secondary amines and their adducts, cyanamide, dicyandiamide, polycarboxylic acids, anhydrides of polycarboxylic acids, polyamines, polyaminoamides, polyadducts of amines and polyepoxides and polyols.

Other suitable hardeners are anhydrides of polycarboxylic acids, typically phthalic anhydride, nadic anhydride, methylnadic anhydride, methyltetrahydrophthalic anhydride, methylhexahydrophthalic anhydride and, in addition, tetrahydrophthalic anhydride and hexahydrophthalic anhydride.

Phenolic resins comprise resole phenolic resins and novolac phenolic resins. Resole phenolic resins may be formed by the reaction of phenol or substituted phenols with an excess of formaldehyde in the presence of a basic catalyst. Novolac phenolic resin may be obtained by reacting an excess of phenol or substituted phenols such as, for example, resorcinol, para-substituted phenol such as p-tert-butyl phenol or cresol with formaldehyde in the presence of an acidic catalyst.

Polyester resins comprise base resin and catalyst. The base resin component of the system can include a reactive polymer, or a monomer, or a combination of the two. Suitable reactive polymers include, but are not limited to, unsaturated polyesters, vinyl esters, and hybrid epoxy-polyester and acrylate-polyester systems that polymerize by way of a free radical mechanism. Suitable monomers include, but are not limited to, styrene, vinyl toluene, other methyl styrene monomers, methyl methacrylate, and other acrylate monomers. Suitable peroxide catalysts include, but are not limited to, ketone peroxides, cumyl hydroperoxides, dibenzoyl peroxides, peroxyesters, peroxyketals, and peroxydicarbonates. Suitable ketone peroxides include, but are not limited to, methyl ethyl ketone peroxide, 2,4-pentadione peroxide, methyl isobutyl ketone peroxide, acetyl acetone peroxide, cyclohexanone peroxide.

Examples of suitable aminoplast condensates include those of urea, dicyandiamide, melamine or oxami de and aldehydes, such as formaldehyde, acetaldehyde, isobutyraldehyde, hydroxypivaldehyde, crotonaldehyde, hydroxyacetaldehyde, furfurol, hydroxymethylfurfurol, glyoxal and glucose. Among the suitable aminoplasts there also may be mentioned condensation products of urea and formaldehyde, urea and glyoxal, urea and acetaldehyde, urea and isobutyraldehyde, urea and crotonaldehyde, urea and hydroxypivalaldehyde and 2-oxo-4-methyl-6-ureido-hexahydropyrimidine.

Solids, such as silicas and clays, have been taught in the literature for use as viscosity modifiers in agrochemical formulations to inhibit gravity-driven sedimentation or cream separation by forming a network or gel throughout the continuous phase, thereby increasing the low-shear viscosity, and slowing the movement of small particles, surfactant micelles or emulsion droplets. The colloidal solids of the present invention instead serve as a processing aid to stabilize the droplets containing the resin monomers during cure by adsorbing to the transient liquid-liquid interface, thereby forming a barrier around the curing droplets so that contacting or neighbouring curing droplets are not able to coalesce, irrespective of whether or not the curing droplets have collected in a sediment or a cream layer. It is possible to distinguish the two different functions —rheological modification or emulsion stabilization, by a functional test such as described below. The effectiveness of the colloidal solid in stabilizing the emulsions of curing polymer droplets depends on particle size, particle shape, particle concentration, particle wettability and the interactions between particles. The colloidal solids must be small enough so that they can coat the surfaces of the dispersed curing liquid polymer droplets, and the curing liquid droplets must be sufficiently small for acceptable dispersion stability against sedimentation of the resulting solid polymer particles if the dispersion concentrate containing such particles is diluted for use. The final polymer particles (and hence, the colloidal solids) will also need to be small enough to provide an acceptably even product distribution at the target site. The colloidal solid also must have sufficient affinity for both the liquids forming the dispersed and continuous phases so that they are able to adsorb to the transient liquid-liquid interface and thereby stabilize the emulsion during cure. This wetting characteristic, particle shape and suitability for Pickering-type emulsion stabilization may be readily assessed by preparing a control formulation lacking the colloidal solid as emulsion stabilizer. In such a case the curing liquid polymer droplets coalesce and form a consolidated mass instead of a dispersion of fine solid polymer particles.

In one embodiment, the colloidal solids have a number-weighted median particle size diameter as measured by scanning electron microscopy of 0.01-2.0 microns, particularly 0.5 microns or less, more particularly 0.1 microns or less.

A wide variety of solid materials may be used as colloidal stabilizers for preparing the dispersions of the present invention including carbon black, metal oxides, metal hydroxides, metal carbonates, metal sulfates, polymers, silica and clays. Suitable colloidal stabilizers are insoluble in any of the liquid phases present in preparation of the concentrate formulation. If an agrochemical active ingredient has suitably low solubility in any liquid used to dilute the final composition, and in both the continuous and (transient) dispersed liquid phases, that is below about 100 ppm at room temperature, and can be prepared at a suitable particle size, and has suitable wetting properties for the transient liquid-liquid interface as described above, then it is also possible that this active ingredient can serve as the colloidal stabilizer. Examples of particulate inorganic materials are oxy compounds of at least one of calcium, magnesium, aluminium and silicon (or derivatives of such materials), such as silica, silicate, marble, clays and talc. Particulate inorganic materials may be either naturally occurring or synthesised in reactors. The particulate inorganic material may be a mineral chosen from, but not limited to, kaolin, bentonite, alumina, limestone, bauxite, gypsum, magnesium carbonate, calcium carbonate (either ground or precipitated), perlite, dolomite, diatomite, huntite, magnesite, boehmite, sepiolite, palygorskite, mica, vermiculite, illite, hydrotalcite, hectorite, halloysite and gibbsite. Further suitable clays (for example aluminosilicates) include those comprising the kaolinite, montmorillonite or illite groups of clay mineral. Other specific examples are attapulgite, laponite and sepiolite.

In one embodiment, non-porous particulate inorganic materials are distributed within the polymer particles along with the cyclopropene complex to serve as an optional diffusion barrier. The diffusion barrier is prepared by suspending such materials along with the cyclopropene complex in the non-aqueous curable liquid mixture that is used to prepare the thermoset or thermoplastic resin polymer particles which serve as dispersed phase b). Suitable particulate diffusion barrier materials include carbon black, metal oxides, metal hydroxides, metal carbonates, metal sulfates, polymers, silica, mica and clays. It is possible for the same particulate inorganic material to serve both to stabilize the emulsion and to act as a diffusion barrier.

In one aspect of the invention, the particulate inorganic material is kaolin clay. Kaolin clay is also referred to as china clay or hydrous kaolin, and contains predominantly mineral kaolinite ($Al_2Si_2O_5(OH)_4$), a hydrous aluminium silicate (or aluminosilicate).

In one aspect of the invention, the particulate inorganic material may be surface modified. Surface-modified means that the inorganic particle surface has been modified so as to have reactive groups. The surface of the particles may be modified using a wide variety of chemicals, with the general structure X—Y—Z, in which X is a chemical moiety with a high affinity for the particle surface; Z is a (reactive) chemical moiety with a desired functionality; and Y is a chemical moiety that links X and Z together.

X may be, for example, an alkoxy-silane group such as tri-ethoxysilane or tri-methoxysilane or trichlorosilane, which is particularly useful when the particles have silanol (SiOH) groups on their surface. X may also be, for example, an acid group (such as a carboxylic or an acrylic acid group) which is particularly useful when the particles have basic groups on their surface. X may also be, for example, a basic group (such as an amine group), an epoxy group, or an unsaturated group (such as an acrylic or vinyl group).

Y can be any chemical group that links X and Z together, for example a polyamide, a polyisocyanate, a polyester or an alkylene chain; more suitably it is an alkylene chain; and even more suitably it is a $C_{2\_6}$ alkylene chain, such as ethylene or propylene.

Reactive groups Z can be selected from any groups, and may be different from Y, which can be used to react with a cross-linker.

The type and amount of colloidal solid is selected so as to provide acceptable physical stability of the composition during cure. This can readily be determined by one of skill in the art by routine evaluation of a range of compositions having different amounts of this component. For example, the ability of the colloidal solids to stabilize the composition can be verified by preparing a test sample with the colloidal solid and it can be confirmed that the emulsion of curable droplets is stable and does not exhibit coalescence. Coalescence is apparent by the formation of large droplets visible to the eye, and ultimately by the formation of a layer of liquid monomers within the formulation. Physical stability of the composition during cure is acceptable if no significant coalescence is evident and the solid polymer particles are present as a fine dispersion.

For example, in one embodiment the colloidal solids are employed in an amount of from 1 to 80%, particularly from 4 to 50% by weight of the disperse phase. Mixtures of colloidal solids may be employed.

The following examples illustrate further some of the aspects of the invention but are not intended to limit its scope. Where not otherwise specified throughout this specification and claims, percentages are by weight.

Examples 1-5

A. Formulation Preparation

The ingredients of the dispersed phase are premixed with a shear mixer as described in table 1 below ("HAIP" is a complex of a-cyclodextrin and 1-MCP in the form of a powder. HAIP contains approximately 4.5 wt % 1-MCP. (AgroFresh, Inc., Pa)), 635 Thin Epoxy Resin and 556 Epoxy Hardener (2:1) (Reichhold, Inc., NC). The continuous phase is premixed as in table 1 with low shear mixer. The premixed dispersed phase is added into the premixed continuous phase, and then blended with a high shear mixer for 5-10 min. For accelerating the epoxy curing reaction, the mixed formulation was treated with high temperature (70° C.) for 3 hr. The components of the control example 3 below were simply homogenized in a high shear mixer.

B. MCP Release Rate

The formulation was diluted in water (25 ppm MCP in water) with appropriate emulsifiers (Kinetic, Toximul TA-6, Stepfac 8180 and Toximul 8320, etc) in a bottle with air-tight seal and then stirred. MCP release was monitored by gas chromatography analysis of MCP concentration in the headspace of the bottle.

C. Epinasty Test

The formulation was diluted in water (20 ppm MCP in water) with appropriate emulsifiers (Kinetic, Toximul TA-6, Stepfac 8180 and Toximul 8320, etc), followed by spraying onto tomato plants. Ethephon was applied 1 hour after 1-MCP treatment. The angle of the 3rd petiole to the plants' stem was measured prior to 1-MCP application and again at 24 hr after treatment. Final data is expressed as the average change in angle of 3rd petiole to stem.

TABLE 1

|  | Example 1 | Example 2 | Example 3 |
|---|---|---|---|
| Dispersed Phase | HAIP 5% Epoxy 635 13.4% Hardener 556 6.6% | HAIP 10% Epoxy 635 10% Hardener 556 5% | HAIP 5% |
| Continuous phase | Aerosil R972 5% IsoparV 70% | Aerosil R972 5% IsoparV 69% AL-22 1% | AL-22 0.5% IsoparV 94.5% |

TABLE 1-continued

|  | Example 1 | Example 2 | Example 3 |
|---|---|---|---|
| Average particle diameter (pm) | 85 | 55 | 10 |
| MCP concentration in headspace |  |  |  |
| In 1 hr | 108 ppm | 450 ppm | 12000 ppm |
| In 2 hrs | 201 ppm | 850 ppm | 14000 ppm |
| In 4 hrs | 380 ppm | 1400 ppm | 14000 ppm |
| Epinasty test Change in angle of leaf | Not tested | 11° | 22° |

TABLE 2

Example 4-5

|  | Example 4 | Example 5 |
|---|---|---|
| Dispersed phase | HAIP 5%/0<br>Phenol-formaldehyde resin 20%<br>Phenol sulfonic acid 1% | HAIP 5%<br>Vinylester resin 20% |
| Continuous phase | Aerosil R972 5%<br>IsoparV 69%/0 | Aerosil R972 5%<br>IsoparV 70% |
| MCP concentration in headspace |  |  |
| In 1 hr | 1350 ppm | 452 ppm |
| In 2 hrs | 1470 ppm | 616 ppm |

Examples 1, 2, 4 and 5 illustrate that the compositions of the present invention lead to reduced degradation and loss of 1-MCP from the molecular complex and give improved resistance to stress responses induced by ethylene in comparison with the control of example 3.

Example 6

A. Formulation Preparation

Premix dispersed phase with high shear mixer. Premix the continuous phase with low shear mixer. Add the premixed dispersed phase into the continuous phase, and then mix with high shear mixer for 5-10 min. For accelerating epoxy curing reaction, the mixed formulation was treated with high temperature (70° C.) for 3 hr.

B. Release Rate

The formulation was diluted in water with appropriate surfactant and then kept in shaker. The samples were taken at appropriate time interval. The release rate was monitored by chromatography analysis.

|  | 6 |
|---|---|
| Dispersed phase | HAIP 10%<br>BPA epoxy resin (bisphenol-A diglycidyl ether) 10% |
| Continuous phase | Polyoxypropylene diamine 5%<br>Aerosil R972 5%<br>IsoparV 70% |

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

We claim:

1. A polymer particle, comprising:
   a body formed from a curable or polymerizable thermoset epoxy;
   a complex of α-cyclodextrin and 1-methylcyclopropene dispersed within the body; and
   a colloidal solid emulsion stabilizer on the body.

2. The polymer particle of claim 1, further comprising at least one non-cross-linkable mobile chemical such that the extraction of this chemical from the polymer particle renders the polymer particle porous in a manner that allows the 1-methylcyclopropene diffuse out at a controlled rate.

3. The polymer particle of claim 1, wherein the colloidal solid emulsion stabilizer is an inorganic material.

4. The polymer particle of claim 1, wherein the curable or polymerizable thermoset epoxy comprises bisphenol A epoxy resin.

5. The polymer particle of claim 1, wherein the curable or polymerizable thermoset epoxy comprises phenolic resin.

6. The polymer particle of claim 1, wherein the curable or polymerizable thermoset epoxy comprises aminoplast resin.

7. The polymer particle of claim 1, wherein the curable or polymerizable thermoset epoxy comprises unsaturated polyester or vinylester resin.

8. The polymer particle of claim 1, wherein the curable or polymerizable thermoset epoxy comprises a biodegradable thermoset resin.

9. The polymer particle of claim 1, wherein the curable or polymerizable thermoset epoxy comprises a cured epoxy resin polymer matrix prepared from curing an epoxy resin comprising di-and polyepoxide monomers, prepolymers or blends thereof with a hardener comprising primary and secondary amines and their adducts, cyanamide, dicyandiamide, polycarboxylic acids, anhydrides of polycarboxylic acids, polyamines, polyamino-amides, polyadducts of amines and polyepoxides, polyols or mixtures thereof.

10. The polymer particle of claim 1, wherein the body has a size of 1-200 microns.

* * * * *